United States Patent
Richardson et al.

[11] Patent Number: 5,817,365
[45] Date of Patent: Oct. 6, 1998

[54] PRODUCTION OF RUBBER ARTICLES, SUCH AS GLOVES

[76] Inventors: Margaret Pamela Richardson; Philip Richardson, both of Maes-y-Coed, Meidrim, St. Clears, Carmarthen, United Kingdom, SA33 5QA

[21] Appl. No.: 404,360

[22] Filed: Mar. 15, 1995

Related U.S. Application Data

[63] Continuation-in-part of Ser. No. 83,634, Jun. 28, 1993, Pat. No. 5,524,294, which is a continuation-in-part of Ser. No. 678,307, Apr. 22, 1991, Pat. No. 5,224,221.

[51] Int. Cl.$^6$ ........................................................ B28B 1/38
[52] U.S. Cl. .............................. 427/7; 427/340; 264/300; 264/305; 264/307; 264/308; 2/167; 2/168; 428/916
[58] Field of Search ...................... 428/911, 916, 428/493; 2/168, 167, 7; 427/340; 264/300, 305, 307, 308

[56] References Cited

U.S. PATENT DOCUMENTS

| 3,633,216 | 1/1972 | Schonholtz . |
| 3,852,826 | 12/1974 | Schindler . |
| 4,696,065 | 9/1987 | Elenteny . |
| 4,851,266 | 7/1989 | Momose et al. . |
| 5,335,373 | 8/1994 | Dangman et al. . |
| 5,486,322 | 1/1996 | Fuchs . |

Primary Examiner—Marion E. McCamish
Assistant Examiner—Elizabeth M. Cole
Attorney, Agent, or Firm—Kohn & Associates

[57] ABSTRACT

Rubber articles are produced by applying a first latex to a former and then applying either a second latex, or a separation material followed by a latex which may be the same as, or different to, the first latex, curing both latices, and removing both layers jointly, so as to make an article with an outer translucent layer and an inner darker layer, with capillary action permitted between the layers.

44 Claims, 1 Drawing Sheet

PRODUCTION OF RUBBER ARTICLES, SUCH AS GLOVES

This is a continuation-in-part of Ser. No. 08/083,634 filed on Jun. 28, 1993, now U.S. Pat. No. 5,524,294, which is a continuation-in-part of 07/678,307 filed on Apr. 22, 1991, now U.S. Pat. No. 5,224,221.

FIELD OF THE INVENTION

The present invention is concerned with production of rubber articles, such as gloves or the like.

BACKGROUND OF THE INVENTION

For many rubber articles, such as protective gloves, it is desirable to provide a visual indication that the article has been breached or suffered accidental damage. Protective gloves are worn by surgeons in the course of surgical operations and are increasingly worn by other medical personnel (such as nurses, dentists and paramedics), and other emergency workers, because of growing concerns over cross-infection associated with diseases such as hepatitis B and acquired immune deficiency syndrome (AIDS).

The basic rationale behind the use of such gloves is that they should provide a complete barrier between the medical or emergency worker and the patient. Unfortunately, there is a risk of damage to the gloves by the use of sharp instruments such as scalpels, needles and the like; such damage is not always immediately detectable.

Further problems often experienced during production and use of such multi-layer articles is that the individual layers adhere to adjacent layers which can be detrimental to certain properties of the articles, and it is generally difficult to detect breach of the articles during manufacture thereof.

It is an object of the invention to provide a method of production of such tamper- or damage-indicating members.

SUMMARY OF THE PRESENT INVENTION

There is provided by the present invention a method of producing a rubber article, which method comprises:

a) applying a liquid containing an elastomer to a former having a release surface so as to form a first body;

b) applying a separation material to at least part of the surface (for example, by halogenation of the surface) of the elastomer present on the former;

c) applying a liquid containing an elastomer onto the separation material present on said first body on the former to form a further body at least partly covering said first body;

d) at least partly curing said elastomers; and e) removing said bodies jointly from said former, so as to provide an article having an outer layer of translucent material and an adjacent inner colored layer of darker color than the outer layer, with said separation material therebetween, said separation material being such as to permit capillary action between said outer layer and said inner layer on breach of one or both of said layers.

The step of removal of the bodies from the former generally involves eversion of the glove-shaped bodies, such that the first applied body becomes the outer body and the second applied body becomes the inner body when both have been stripped from the former.

According to a first embodiment of the present invention, the rubber article comprises a glove. According to a second embodiment, the rubber article comprises a condom, or a closed end portion of a condom. It may be preferred that the whole condom comprises inner and outer layers as hereinbefore described; alternatively it may be preferred that it is only the closed end portion of the condom which is two-layered. It is appreciated that the present invention has further applications in respect of other dipped multi-layer rubber articles, such as finger cots or the like.

Judgement by eye of the difference between lighter and darker shades of color is generally straightforward. However, if needed, guidance can be gained from the international system of color definition known as the "NCS". The NCS is described in the "ICI Colour Dimensions Colour Atlas" published by Imperial Chemical Industries Plc of London in 1986 ("Colour Dimensions" is a registered trade mark of Imperial Chemical Industries). The NCS defines color in terms of a cypher, the first two digits of which extend from 00 to 99, with 00 representing white (that is, the ultimate lightness) and 99 representing black with the intermediate values from 01 to 98 representing increasingly darker shades. Lighter shades therefore have a lower pair of first digits. It is preferred that the outer layer has an NCS value at least 10 units lower than that of the inner layer.

It may be preferred that the separation material comprises a gelatinous medium such as a hydrogel or a resinous emulsion. The gelatinous medium may contain a coagulant such as calcium chloride or calcium nitrate or the like, and/or particulate solid material such as calcium carbonate.

Such a coagulant may contain a dispersion of one or more ingredients present in the elastomeric latex of one or more of the bodies. Typical such ingredients include micronised sulfur, zinc oxide or other similar finely divided solid material, and may advantageously further comprise a film-forming polymeric stabiliser or binder such as polyvinyl acetate or the like (in order to inhibit generation of particulates on damage to the rubber article). These ingredients, when present in the coagulant, may advantageously comprise one or more of the facing surfaces of the bodies, in such a way as to effect separation of the bodies and allow liquid penetration therebetween. The coagulant may contain a non-film forming particulate material, such as diatomaceous earth, bentonite or the like, suitable for enhancing the required separation of the bodies.

Preferably the separation material may comprise a water-absorbent particulate mineral medium, such as calcium carbonate, Celite (a material commercially available under the trade mark Lytron 820 from Manville-Schurer Corp), diatomaceous earth or the like. The use of the above-described particulate materials is advantageous because of their adhesion to the latices of the bodies, their water absorbent properties and interlocking structure being believed to obviate release thereof from a resulting article in the case of rupture of one or both of the bodies.

The method according to the invention may advantageously involve application of one or more latex modifying agents to at least part of the surface of one or both of the bodies. The agent may be present in a coagulant of the separation material; alternatively it may be applied directly to a body.

A preferred latex modifying agent comprises cetyl pyridinium chloride, the use of which is also advantageous because of the anti-viral properties thereof. It is sometimes preferred that the cetyl pyridinium chloride is applied in an alcoholic solution to at least part of the surface of a body.

The latex modifying agent may alternatively comprise an exudate which has migrated from the bulk of an elastomeric latex, of one or both of the bodies, to the surface thereof by the process of syneresis. At least one of the elastomeric latices may be selected so as to include a suitable exudate. Alternatively, the method may include impregnating at least one of the latices with a suitable exudate, such as an emulsion of a low molecular weight wax, a pH dependent chemical solution or the like. Preferably the method includes drying of the bodies, so as to permit migration of the exudate to the surface of at least one of the bodies.

Advantageously, the method involves a prevulcanisation stage, which is beneficial in optimizing the desired properties of the resultant article, such as wet gel strength, on-mold shrinkage, moisture retention during vulcanization, physical strength and the like. The prevulcanization step preferably involves monitoring of the swelling index of the latices in order to enable optimization of the above properties.

In a preferred embodiment of the invention, the method may involve respective prevulcanization of the first and second bodies to varying extents. Typically the latex material of the inner body (in use) may have a swelling index of about 1.8, whereas that of the outer body may have a swelling index of about 2.1; however variance of these values may be made to achieve optimum separation between the layers.

The lower the swelling index, the greater the level of the cross-linkage of the latex; a high level of cross-linkage gives rise to an increased level of syneresis as described above.

It is preferred that the separation material is applied as a substantially discontinuous layer to the first body. The nature of the separation material is preferably such that the elastomeric bodies preferentially adhere to the separation material rather than to each other; such preferential adherence promotes air gap formation between the layers and enhances detection of any liquid penetration between the layers. It is further preferred that the separation material can act as a release agent which eases separation of the inner and outer layers.

The separation material may in some embodiments include an anti-bacterial or anti-viral material, such as the material commercially available under the trade mark Nonoxynol 9.

It is preferred that the resulting article is substantially free of any calorimetric indicator material which would be responsive to the penetration of body or any other fluids between the layers. Any visual detection of damage or breach of the article by body or other fluids is due to capillary action between the two layers which causes the inner layer to become substantially contiguous with the outer layer in the area of breach such that the perceived color is that of the inner layer.

The liquid containing an elastomer is generally applied to the former by dipping, although other methods aimed at substantially complete coverage of the former (such as spraying or the like) may be used in some instances. The liquid is typically a rubber latex, which may be applied to the former after application of a coagulant to a former.

After application to the former, the elastomeric membrane thus produced is generally dipped in one or more baths, such as further coagulant, water wash, vulcanization bath and an optional further coating, such as a lubricant or hydrogel.

The outer layer of the finished article is of a translucent material and has a contrasting color relative to the inner layer. Preferably the inner layer should be of substantially uniform coloration throughout. Typically, the outer layer may be of yellow or white translucent material and the inner layer of a darker color, such as green, black or the like.

The former is typically of porcelain or the like, as is conventionally used for dip-forming rubber articles. It may be preferred that at least a portion of the surface of the former is of a dark color which allows the integrity of a translucent elastomeric layer present on the former to be tested in situ.

If a perforation, puncture or small rupture arises which communicates between the outer and inner surfaces of the translucent layer, the liquid contacting the layer's outer surface may pass through the perforation and contact with the outer surface of such a porcelain former, thereby giving a change in the perceived color from pale (the translucent layer) to dark (the colored former).

The inner and outer layers of the rubber article may be sealed together in the method according to the invention; when such sealing is employed it is preferably at or near an open end region of the article, the sealing preferably being such that a substantial portion of the outer layer is substantially unbonded to the inner layer.

The present invention further comprises a method of producing a rubber article, which method comprises:

a) applying a first elastomeric latex to a former having a release surface so as to form a first body;

b) applying a second distinct elastomeric latex to said first body on said former so as to c) at least partly curing said elastomers; and d) removing said bodies jointly from said former, so as to provide an article having an outer layer and an adjacent inner layer, said elastomeric latices having adhesion to one another less than their cohesiveness, so as to induce formation of a capillary layer between said outer layer and said inner layer, the coloration of the inner and outer layers being substantially as hereinbefore described.

The first and second elastomeric latices are typically respectively prepared by combining differing specifications of latex and coagulant so as to provide inner and outer layers having the above described adhesive properties. Typically the coagulant type and medium for each layer will be different.

It is preferred that the method further comprises providing a separation material between the layers substantially as hereinbefore described.

According to a further aspect of the present invention, there is provided a damage-indicating rubber article which comprises an inner layer and an outer layer, at least a portion of said outer layer being sealed to said inner layer so as to surround a zone of the surface of said inner layer which is not sealed to said outer layer, thereby forming a space between said layers which is adjacent said zone and is substantially free of air, both said layers being of substantially liquid and air-impermeable material, said outer layer being of translucent material at least in the area thereof overlying said zone and having a contrasting color relative to the color of said inner layer, such that when there is a breach in either layer adjacent said zone there is a change in perceived color in the area of breach, and a separation material is arranged between said layers so as to be capable of forming a separable coating on either of said layers, and is such as to permit capillary action between said inner and outer layers on breach of one or both of said layers.

It is preferred that in the above-mentioned zone, both the outer and the inner layer should be of substantially uniform coloration throughout. Typically, the outer layer may be of yellow or white translucent material and the inner layer of a darker color, such as green, black or the like.

The perceived color when the article is undamaged is that of the outer layer, but when damage has taken place, and in the presence of an aqueous liquid (such as blood or the like), a capillary action takes place between two layers such that the perceived color is that of the inner layer spreading from the area of the breach.

It is preferred that the inner and outer bodies are each of flexible, liquid- and air-impermeable material, and are sealed together at or near an open end region of the article, a substantial proportion of the outer surface of the inner body being substantially unbonded to the inner surface of the outer body. In this embodiment of the invention, the outer body is preferably wholly of translucent material. The inner body may be strongly colored, for example, of black, luminous yellow or green.

We have found that it is particularly advantageous for the inner layer (and/or the outer layer) to contain a fluorescent or luminescent pigment, which can be excited by one or more wavelengths of light employed in a light source in, for example, an operating theatre or the like.

According to this aspect of the present invention, therefore, there is provided medical apparatus comprising in combination:

(a) a damage-indicating glove as described above, in which the above-mentioned zone is substantially darker in color than the outer layer and contains a fluorescent or luminescent pigment: and (b) illumination means for illuminating an operating environment, the illumination means and the pigment being selected such that the pigment is excited by one or more wavelengths of light emitted by the illumination means.

It is particularly preferred that the illumination means comprises a fluorescent light source of the type generally referred to as artificial daylight; such a light source emits visible light throughout substantially the entire visible spectrum and also in the near ultra-violet spectrum.

The fluorescent or luminescent pigment is preferably one which absorbs radiation in the near ultra-violet wavelength range, and emits light in the visible range in order to provide enhanced visibility for the inner layer, in the area of breach, when fluid has entered into the space between the respective layers.

There is further provided by the present invention a rubber article which comprises an inner layer and an outer layer, at least a portion of the outer layer being sealed to the inner layer so as to surround a zone of the surface of the inner layer which is not sealed to the outer layer, thereby forming a space between said layers which is adjacent the zone, both the layers being of substantially liquid- and air-impermeable material, the outer layer being of translucent material at least in the area thereof overlying the above-mentioned zone and having a contrasting color relative to the color of the inner layer, such that when there is a breach in either layer adjacent the above-mentioned zone there is a change in perceived color in the area of breach, the inner and outer layers being respectively formed from distinct first and second elastomeric latices, the elastomeric latices having adhesiveness to one another less than their cohesiveness so as to permit capillary action between the inner and outer layers.

Capillary action then causes the liquid to move radially outwards from the perforation point between the inner surface of the (outer) layer of translucent material and the outer surface of the adjacent layer, creating a "wet zone" between the two layers. Due to the optical quality of the layer of translucent material and the dark color of the adjacent layer, the "wet zone" surrounding the perforation point will be perceived as having a different color to the rest of the layer since the darker color of the inner layer will be visible in the "wet zone".

Any perceived color change which results may be detected upon visual inspection. Alternatively, the perceived color change may be detected by an appropriate optical/electronic sensor arrangement, such as a closed circuit television (or charge coupled cameras) coupled to microprocessor or computer control circuitry, which sensor arrangement is tuned to react to optical wavelengths corresponding to the optical wavelength of the perceived changed color in the "wet zone".

Any such perceived color change may be enhanced by the provision of a fluorescent or luminescent pigment for the inner layer (and/or for the outer layer), and illumination means for illuminating an operating environment, the illumination means and the pigment being selected such that the pigment is excited by one or more wavelengths of light emitted by the illumination means.

There is provided by the present invention a method of producing a glove, which method comprises:

(a) dip forming an elastomeric latex on a hand-shaped former to form a first glove-shaped uncured body;

(b) surface halogenating (e.g. chlorinating) at least part of the dip-formed elastomeric material present on the former;

(c) dip-forming a further elastomeric latex onto the halogenated glove-shaped body to form a further uncured body surrounding the halogenated body; and (d) removing the two bodies jointly from the former, the elastomeric latices being such that the resulting glove-shaped member has an outer layer of a translucent material with a contrasting color relative to the color of the inner layer.

The halogenation is preferably controlled to substantially avoid adhesion in the halogenated area; in order to obtain a glove according to the above-mentioned embodiment of the invention in which the inner and outer layers are secured to one another by the resilience of the outer layer, the first uncured body may be halogenated all over the surface thereof. When the two bodies are then removed jointly from the former, they separate (or delaminate) from one another.

For some applications, more than two glove-shaped bodies may be provided, one inside the other; these bodies may be sealed together at or near the wrist-engaging edges thereof. Alternatively, the outer body of such a multi-layer construction may be secured by its inherent resilience, as described above with reference to a two-layer construction.

DETAILED DESCRIPTION OF THE DRAWINGS

Preferred embodiments of the invention will now be described by way of example only with reference to the accompanying drawings, wherein.

Figure 1:
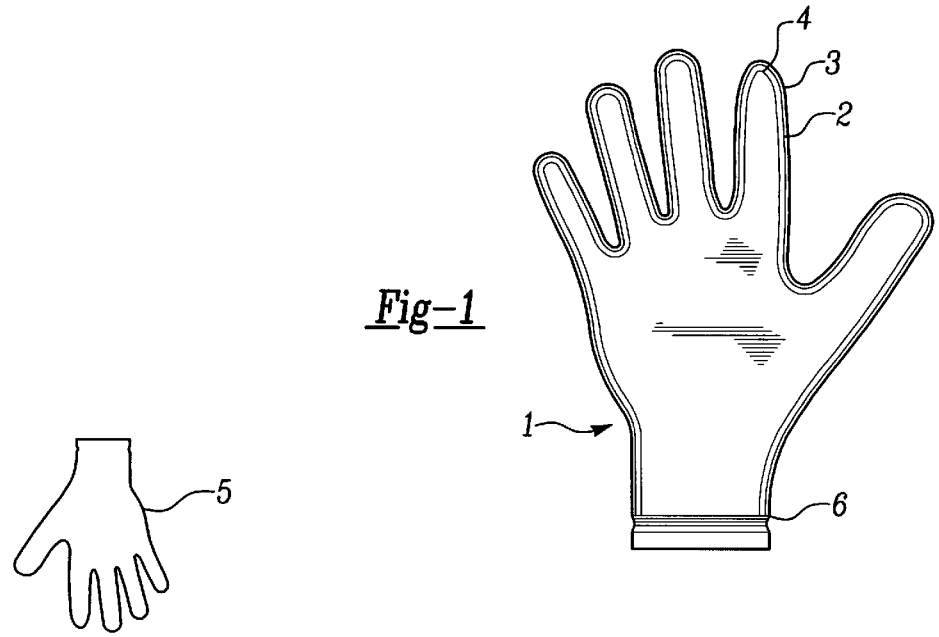
FIG. 1 is a sectional view of an exemplary glove according to the invention.

Referring to FIG. 1, there is illustrated a glove indicated generally by the reference numeral 1, which comprises an inner glove 4 of latex, which may be highly colored, for example, of black, luminous yellow, or green. The outer surface of inner glove 4 may be smooth or may have a fine textured finish. An outer (translucent) glove 3 of contrasting color relative to the inner glove is of the same shape and size as the inner glove and is a close fit thereon and sealed thereto at the wrist portion 6. Between the inner glove 4 and outer glove 3 is a separation layer 2 which keeps the two gloves separated from each other. At or near the edges of the gloves 4,3 which engage the wearer's wrist, the gloves 4,3 may be sealed together. The space between the gloves 4,3 is substantially evacuated of air, so that the adjacent surfaces of the gloves 4,3 are pressed firmly against the separation material which is situated between the two gloves, the inner and outer gloves 4,3 act as a single glove.

However, if a small puncture or leak is made in either of the gloves 4,3 in the presence of aqueous liquids such as blood or body fluids, a color change in the vicinity of the puncture becomes apparent, indicating the existence of the puncture or leak. At the same time, the outer glove 3 becomes relatively more mobile over the inner glove 4 in the vicinity of the puncture, causing a detectable change of feel of the glove.

An anti-bacterial or anti-viral substance may be present in the space between the gloves 4,3 to act against any viral material which penetrates into the space.

For some applications, more than two gloves 4,3 may be provided, one inside the other, all sealed together at the wrist-engaging edges and having the spaces between the gloves air-free.

Figure 2:
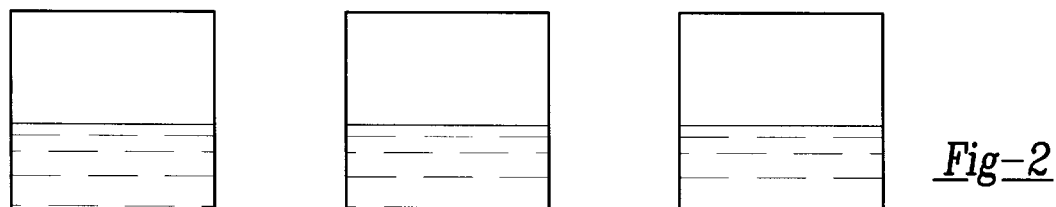
FIG. 2 is a diagrammatic illustration of the sequence of operations in a method according to the invention.

FIG. 2 is a diagrammatic illustration of the production of the latex glove as described above. A porcelain former 5 is dipped into a first container 7 of latex so as to form the first layer of the glove 1. The former 5 is then dipped into a second container having therein a separation material, such as calcium carbonate or diatomaceous earth. The former 5 is then dipped into a further container 9 of latex, thereby forming a second latex layer on the outside of the separating material 2. The latex layers are then cured, and further water washed, vulcanized and optionally treated with a lubricant (not shown). The inner layer on the form is translucent, in contrast to the darker outer layer. The inner and outer layers respectively, are then sealed at the end nearest the wrist portion of the glove 1. Because the glove 1 as a result of the method is formed inside out on the former 5, it must then be everted. Therefore the outer layer becomes inner glove 4 and the inner layer becomes outer glove 3.

Figure 3:
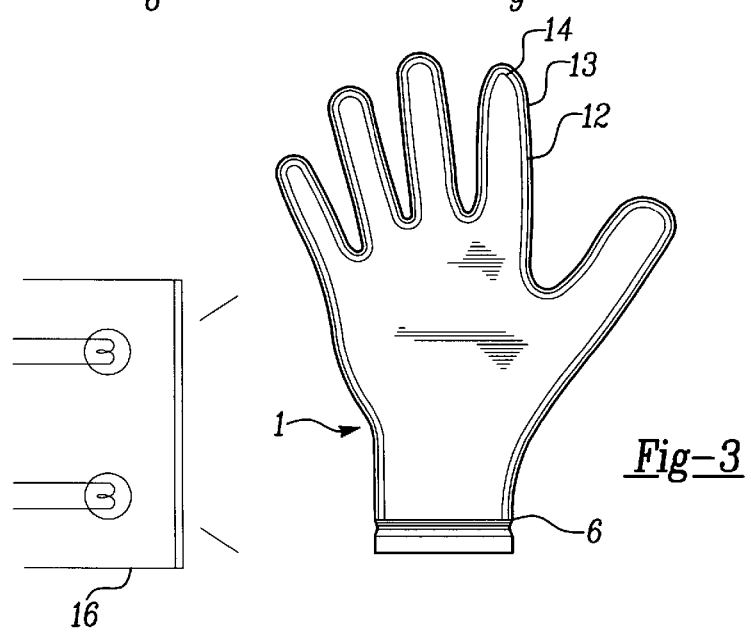
FIG. 3 is an illustration of a preferred embodiment of the invention.

Referring to FIG. 3, there is shown apparatus which is suitable for use in, for example, operating theaters to indicate breaches in the glove 1. The apparatus comprises a light source 16 which illuminates the theater. The inner layer 14 of the glove contains a fluorescent pigment such that when the glove is breached by a scalpel or the like, in the presence of an aqueous liquid, the pigment is excited on exposure to the light source, causing illumination in the area of breach, which is easily visible to the surgeon or other personnel in the operating theater.

What we claim is:

1. A method of producing a rubber article, which method comprises:
   (a) applying a liquid containing a translucent elastomer to a former having a release surface thereon so as to form on said surface a first body of said elastomer, said first body having a first color and an outer surface;
   (b) applying a separation material whilst said first body is in an uncured state, to at least part of said outer surface, while said first body is present on said former;
   (c) applying a liquid containing an elastomer onto the separation material present on said first body on said former to form a second body of a second color, said second color being darker than said first color, said second body at least partly covering said first body;
   (d) at least partly curing said elastomers while said first and second body are on said former; and
   (e) removing said first and second bodies jointly from said former, such that said first and second bodies are everted during said removal, whereby said first and second bodies comprise an article having an outer layer of translucent material and said first color, and an adjacent inner layer of said second color, with said separation material between said outer layer and inner layer, said separation material being such as to permit capillary action between said outer layer and said inner layer on breach of at least one of said layers.

2. A method according to claim 1, wherein said first body has an NCS value at least 10 units lower than that of said second body.

3. A method according to claim 1, wherein said separation material comprises a gelatinous medium.

4. A method according to claim 3, wherein said separation material contains a coagulant.

5. A method according to claim 4, wherein said coagulant comprises calcium chloride or calcium nitrate.

6. A method according to claim 5, wherein said coagulant further comprises particulate solid material.

7. A method according to claim 6, wherein said particulate solid material comprises calcium carbonate.

8. A method according to claim 4, wherein said coagulant is selected from the group consisting of micronised sulfur, finely divided zinc oxide and a film-forming polymeric stabiliser or binder.

9. A method according to claim 8, wherein said binder comprises polyvinyl acetate.

10. A method according to claim 4, wherein said coagulant contains a non-film forming particulate material.

11. A method according to claim 10, wherein said non-film forming particulate material comprises diatomaceous earth or bentonite.

12. A method according to claim 1, wherein said separation material comprises a water-absorbent particulate mineral medium.

13. A method according to claim 12, wherein said water-absorbent particulate mineral medium is selected from the group consisting of calcium carbonate, or diatomaceous earth.

14. A method according to claim 1, which further comprises applying at least one latex modifying agent to at least part of the surface of at least one of said bodies.

15. A method according to claim 14, wherein said latex modifying agent comprises cetyl pyridinium chloride, applied in an alcoholic solution to at least part of the surface of one of said bodies.

16. A method according to claim 14, wherein said latex modifying agent comprises an exudate which has migrated from one or both of said bodies, to a surface of said body by the process of syneresis.

17. A method according to claim 16, which includes impregnating at least one of said elastomeric latices with said exudate.

18. A method according to claim 16, wherein said exudate comprises an emulsion of a low molecular weight wax.

19. A method according to claim 16, which further comprises drying said bodies, so as to permit migration of said exudate to the surface of at least one of said bodies.

20. A method according to claim 1, which further comprises a prevulcanization step prior to applying the liquids to the former which prevulcanization step includes monitoring of the swelling index of said elastomers.

21. A method according to claim 20, wherein said method comprises respective prevulcanization of said first and second bodies each to a different extent.

22. A method according to claim 21, wherein the elastomer of said inner body has a swelling index of approximately 1.8 and the elastomer of said outer body has a swelling index of approximately 2.1.

23. A method according to claim 1, wherein said separation material is applied as a substantially discontinuous layer to said first body.

24. A method according to claim 23, wherein said separation material includes an anti-bacterial or anti-viral material.

25. A method according to claim 1, wherein said rubber article is substantially free of any calorimetric indicator material which would be responsive to the penetration of body or any other fluids between said layers.

26. A method according to claim 1, wherein either of said liquids containing an elastomer is applied to the former by dipping.

27. A method according to claim 26, wherein either of said liquids is a rubber latex, which is applied to said former after application of a coagulant to said former.

28. A method according to claim 26, wherein after application to said former, said first and second bodies on said former are dipped in one or more baths comprising a further coagulant, water wash or vulcanization bath.

29. A method according to claim 28, wherein said bodies on said former are dipped in a further coating of a lubricant or hydrogel.

30. A method according to claim 1, wherein said second color is substantially uniform throughout said inner layer.

31. A method according to claim 29, wherein said first color is selected from the group consisting of yellow and white.

32. A method according to claim 31, wherein said second color is selected from the group consisting of green and black.

33. A method according to claim 1, wherein said former is of porcelain.

34. A method according to claim 33, wherein at least a portion of the surface of said former is of a dark color.

35. A method according to claim 1, wherein said inner and outer layers of said rubber article are sealed together.

36. A method according to claim 35, wherein such sealing is adjacent an open end region of said article.

37. A method according to claim 35, wherein said sealing is such that a substantial portion of said outer layer is substantially unbonded to said inner layer.

38. A method according to claim 1, wherein said rubber article comprises a glove.

39. A method according to claim 1, wherein said rubber article comprises a condom, or a closed end portion of a condom.

40. A method according to claim 39, wherein the whole condom comprises inner and outer layers.

41. A method according to claim 39, wherein the closed end portion of said condom is double-layered.

42. A method of producing a rubber article, which method comprises:

a) applying a translucent elastomeric latex to a former having a release surface thereon, so as to form on said surface a first translucent body of said latex, said first body having a first color and an outer surface;

b) applying a second elastomeric latex onto said first body present on said former to form a second body of a darker color and at least partly covering said first body;

c) at least partly curing said elastomeric latex while said first and second bodies are on said former; and d) removing said first and second bodies Jointly from said former, such that said first and second bodies are everted during said removal, whereby said first and second bodies comprise an article having a translucent outer layer and said first color, and an adjacent inner layer of darker color than said outer layer, said elastomeric latices having adhesion to one another less than their cohesiveness, so as to induce formation of a capillary layer between said outer layer and said inner layer.

43. A method according to claim 42, wherein said first and second elastomeric latices each include a coagulant and each respectively comprise a different latex and coagulant.

44. A method according to claim 42, which further comprises providing a separation material between the layers.

* * * * *